(12) United States Patent
Valtchev

(10) Patent No.: US 8,495,809 B2
(45) Date of Patent: Jul. 30, 2013

(54) VAGINAL DELINEATING DEVICE

(76) Inventor: Konstantin Lazarov Valtchev, Toronto (CA)

(*) Notice: Subject to any disclaimer, the term of this patent is extended or adjusted under 35 U.S.C. 154(b) by 579 days.

(21) Appl. No.: 12/657,437

(22) Filed: Jan. 21, 2010

(65) Prior Publication Data

US 2010/0180422 A1   Jul. 22, 2010

Related U.S. Application Data

(63) Continuation-in-part of application No. 12/080,848, filed on Apr. 8, 2008, now Pat. No. 8,347,888.

(51) Int. Cl.
*B21D 39/03* (2006.01)
*B23P 11/00* (2006.01)

(52) U.S. Cl.
USPC .............. 29/428; 606/119; 128/833; 128/839

(58) Field of Classification Search
USPC .................. 606/119; 128/830, 833, 834, 835, 128/838, 839, 840; 29/428
See application file for complete search history.

(56) References Cited

U.S. PATENT DOCUMENTS

| | | | | |
|---|---|---|---|---|
| 3,877,433 A | * | 4/1975 | Librach | 606/119 |
| 4,022,208 A | * | 5/1977 | Valtchev | 604/515 |
| 5,100,382 A | * | 3/1992 | Valtchev | 604/102.02 |
| 5,382,252 A | * | 1/1995 | Failla et al. | 606/119 |
| 5,394,863 A | * | 3/1995 | Sanford et al. | 600/199 |
| 5,445,643 A | * | 8/1995 | Valtchev | 606/119 |
| 5,520,698 A | * | 5/1996 | Koh | 606/119 |
| 5,562,679 A | * | 10/1996 | Valtchev | 606/119 |
| 5,840,077 A | * | 11/1998 | Rowden et al. | 606/119 |
| 5,928,249 A | * | 7/1999 | Saadat et al. | 606/119 |
| 6,706,026 B1 | * | 3/2004 | Goldstein et al. | 604/278 |
| 2005/0107818 A1 | * | 5/2005 | Valtchev | 606/193 |
| 2009/0131954 A1 | * | 5/2009 | Christian et al. | 606/119 |

* cited by examiner

*Primary Examiner* — David Bryant
*Assistant Examiner* — Christopher Koehler
(74) *Attorney, Agent, or Firm* — Sturm & Fix LLP

(57) ABSTRACT

A gynecological instrument for delineating the fornix of the vagina during laparoscopic operations having a solid ring with a guiding groove for easy and safe opening of the vagina laparoscopically. The solid ring has a protrusion outward which pushes the vaginal wall toward the peritoneal cavity, creating a bulging of the vaginal wall, making it easily identifiable. The solid ring is permanently attached to the proximal end of the base by a semi-cylindrical wall which creates a window anteriorly, for better visualization of the cervix and easy insertion of a cannula or delineator into the uterine cavity. The vaginal delineator is locked to the head of the uterine mobilizer by inserting the locking end of a cannula, delineator or vaginal delineator lock, through the hole of the delineator and into the head of the uterine mobilizer. An elastic diaphragm is provided with different sizes for obstruction of the vagina, which does not allow flow in any direction. This instrument can be used to mobilize the uterus, to inject dye into the uterus and Fallopian tubes, and to delineate the fornix of the vagina, even when the uterus Has been previously removed.

16 Claims, 13 Drawing Sheets

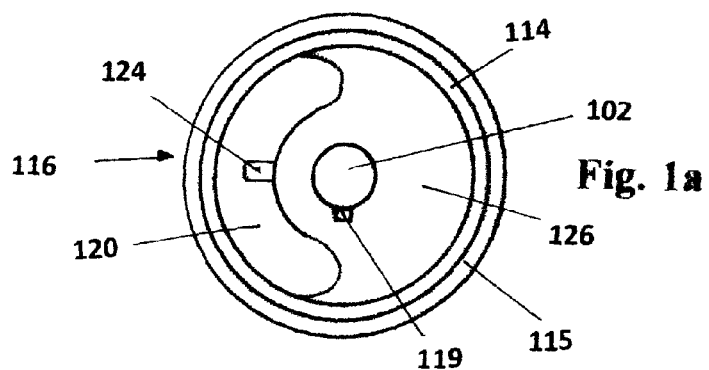
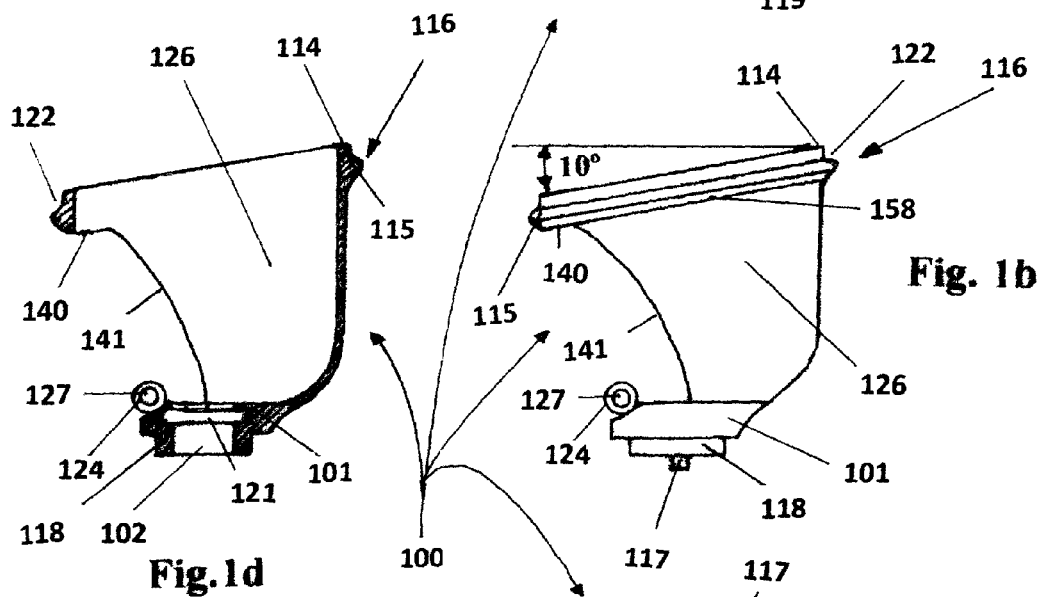
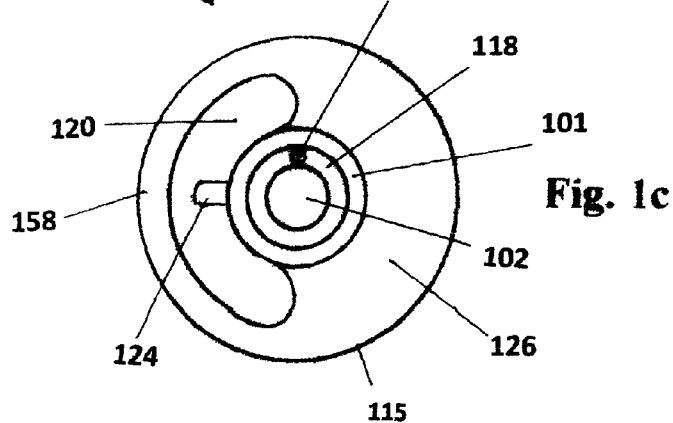

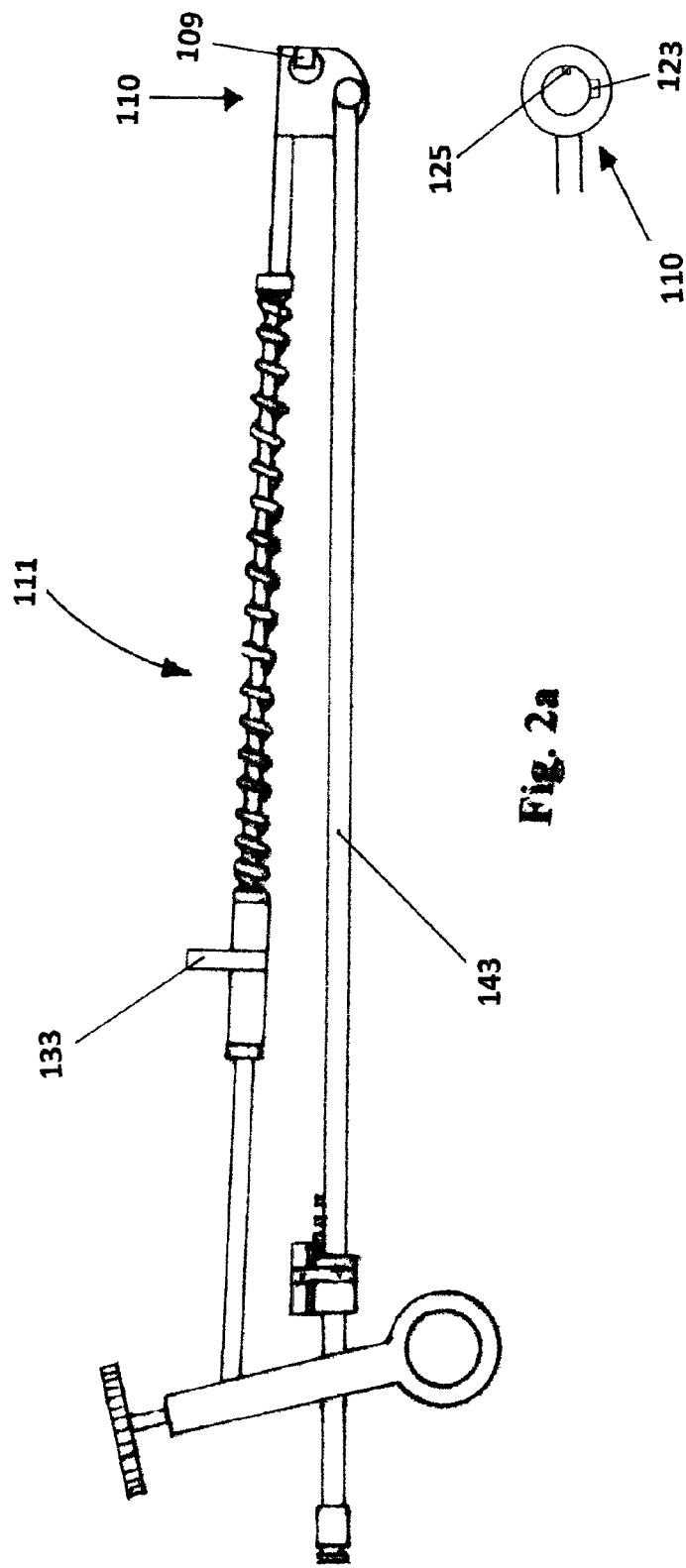

VAGINAL DELINEATING DEVICE

CROSS REFERENCE TO RELATED APPLICATIONS

Continuation-in-part of U.S. Ser. No. 12/080,848, filed Apr. 8, 2008 in the name of Konstantin L. Valtchev For: "VAGINAL DELINEATING DEVICE", of which the following forms the specification.

BACKGROUND OF THE INVENTION

The present invention relates generally to a gynecological device. More particularly the present invention relates to a vaginal delineating device for use with the Valtchev® Uterine Mobilizer, as disclosed in U.S. Pat. No. 5,562,679, which is hereby incorporated by reference. Hysterectomy is a surgical procedure for removal of a part or the whole of the uterus. Subtotal Abdominal Hysterectomy (SAH) and Total Abdominal Hysterectomy (TAH) are performed through an incision in the lower part of the abdomen. Total Hysterectomy can also be performed vaginally, and is named—Vaginal Hysterectomy.

Since the introduction of laparoscopic surgery, hysterectomy can be performed Laparoscopically: Total Laparoscopic Hysterectomy (TLH), Subtotal Laparoscopic Hysterectomy (SLH) or by combining laparoscopic and vaginal approach—Laparoscopically Assisted Vaginal Hysterectomy (LAVH). SLH, TLH and LAVH are usually viewed as more preferable, because they are less invasive compared to Abdominal Hysterectomy. Thus, SLH, TLH and LAVH usually result in shorter hospitalization and recovery time and are associated with less pain and discomfort. Adequate identification of the fornix of the vagina during TLH and LAVH is a problem. Another problem, which has to be addressed is leakage of $CO_2$, when a vagina is opened laparoscopically.

Other problems, not appropriately addressed in the prior art, are: difficult or impossible use of a tenaculum to facilitate insertion into the uterine cavity of an obturator or cannula; absence of a groove, which can guide the cutting instrument, used to open the vagina laparoscopically; lack of an appropriate posterior surface of the delineator, which can play a role as backstop for a laser beam and electrical current used to excise a part of the posterior vaginal wall; existing delineators can not be used without a cannula. There is therefore a need for a vaginal delineating device which will address and solve the above problems.

BRIEF SUMMARY OF THE INVENTION

An objective of the present invention is to provide a vaginal delineating device for use in gynecological laparoscopic procedures, which is attached to the Valtchev® Uterine Mobilizer. The device is comprised of a vaginal delineator which is locked into the head of the uterine mobilizer by inserting through its opening a locking end of a cannula, an obturator or a delineator lock. The vaginal delineator has a solid ring permanently attached to a base by a cylindrical wall. The solid ring has an elliptic shape and is tilted anteriorly about 10°. This makes insertion of the vaginal delineator into the vagina easier. The vaginal delineator has a window anteriorly. The window is one of the important features of this invention. It allows much better visualization of the cervix at the time of insertion of an obturator or cannula into the uterine cavity, it also allows insertion of a tenaculum through the window for grasping and pulling the cervix as far down as possible for easier insertion of an obturator or cannula into the uterine cavity. Instead of a tenaculum for pulling the cervix downward, a suture attached to the cervix can be pulled down through the window, which will bring the cervix down for easy insertion of a cannula or obturator into the uterine cavity. On the outside surface of the solid ring there is a elliptical protrusion. When the vaginal delineator is inserted into the vagina, the elliptical protrusion pushes the vaginal wall at the fornix of the vagina toward the peritoneal cavity, which is well seen trough the laparoscope. A groove, which is created between the rim of the solid ring and the elliptical protrusion, guides the cutting instrument, when the vaginal wall is cut. This makes the cutting easier and safer. Through a hole in the center of the base and its extension is passing the locking end of an obturator, a cannula or a delineator lock. After the locking end passes through the hole it can be inserted and locked into the head of the Valtchev® Uterine Mobilizer. The vaginal delineator can be attached and locked into the head of the uterine mobilizer by a vaginal delineator lock, this eliminates the use of an obturator or cannula. This feature is unique for this device. This allows the delineator to be used alone, if the insertion of an obturator or cannula into the uterine cavity is impossible or not necessary, as it is in case where a patient has had previous subtotal or total hysterectomy. The posterior and lateral parts of the cylindrical wall are solid and play a role as a backstop for a laser beam or electric cutter. The surface of the delineator has two different finishes: in one model it is sand blasted and does not reflect the laser beam in the second model it is mirror polished.

An elastic diaphragm of elastic material such as nylon, silicone, etc., was described in the previous patent application Ser. No. 10/715,104, filed on Nov. 17, 2003, and is presented here as a reference. Its use is to obstruct the vagina and prevent leakage in any direction, when the vagina is opened laparoscopically. The elastic diaphragm has at its center an opening through which an extension of the base is inserted. When the delineator is locked into the head of the mobilizer, the annulus of the elastic diaphragm, is clamped between the head of the mobilizer and the base of the delineator. This prevents leakage in any direction. Advantage of this type of an elastic diaphragm is that it will not leak even if it is punctured. The balloons which are in common use, if they burst, leaking is imminent. There is a loop on the anterior surface of the base of the delineator. Through this loop a suture attached to the cervix can be treaded and tied, which will secure the attachment of the delineator to the cervix. At the end of the colpotomy, the uterus can be pulled out of the vagina by removing the vaginal delineator from the vagina. As well a tenaculum can be attached to the loop and to the tenaculum holder of the Valtchev® Uterine Mobilizer pushing the elastic diaphragm closer to the mobilizer, which eliminates the obstruction of a view through the window of the vaginal delineator. This makes the visualization of the cervix easier, which facilitates the insertion of an obturator or cannula into the uterine cavity.

Other objects, advantages and novel features of the present invention will become apparent from the following detailed description of the invention when considered in conjunction with the accompanying drawings.

BRIEF DESCRIPTION OF THE SEVERAL VIEWS OF THE DRAWINGS

FIG. 1a is a plan view from the top of the vaginal delineator;

FIG. 1b is a side view of the vaginal delineator;

FIG. 1c is a plan view from the bottom of the vaginal delineator;

FIG. 1d is a cutaway view of the vaginal delineator;

FIG. 2a is a side elevation view of the Valtchev® Uterine Mobilizer;

FIG. 2b is a plane view from the top of the head of the Valtchev® Uterine Mobilizer;

DETAILED DESCRIPTION OF THE INVENTION

Figures 3A, 3B, 3C, 3D:
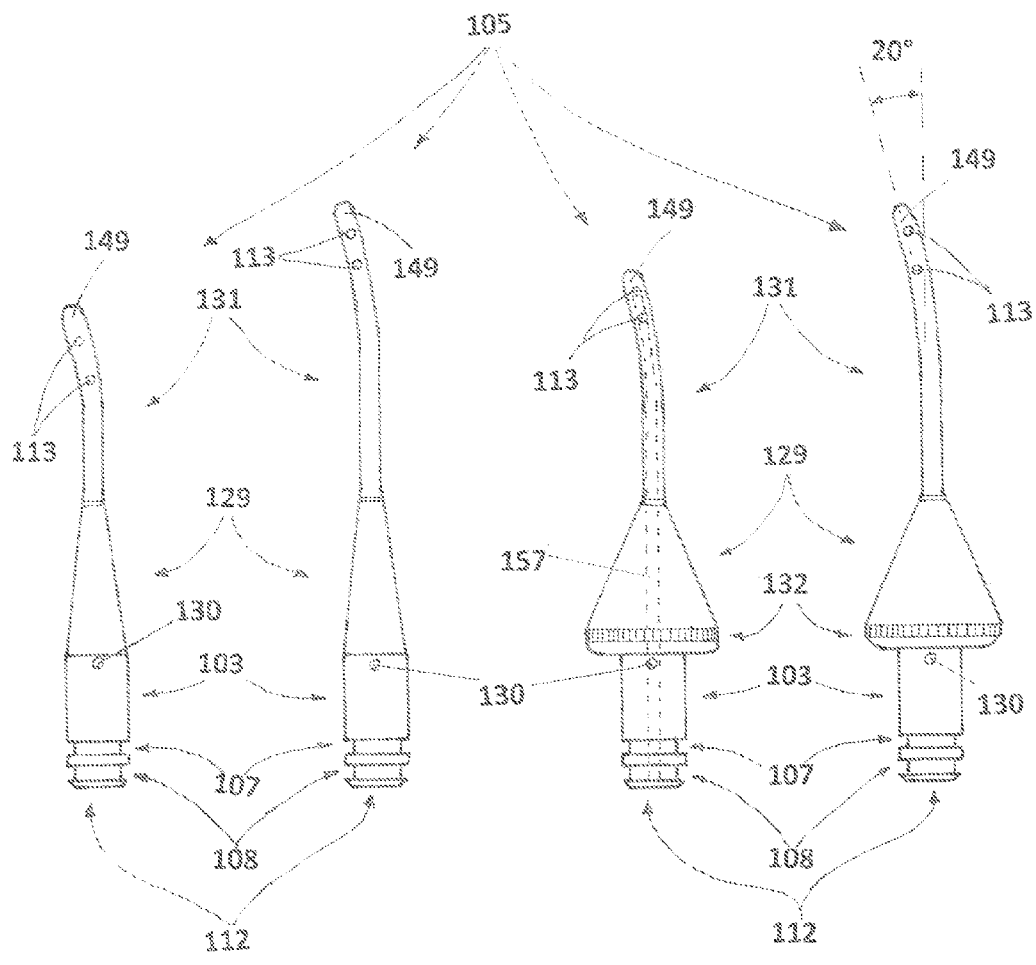
FIG. 3a is a side elevation view of a short cannula with a small cone.
FIG. 3b is a side elevation view of a long cannula with small cone.
FIG. 3c is a side elevation view of a short cannula with large cone.
FIG. 3d is a side elevation view of a long cannula with large cone.
Figures 4A, 4B, 4C, 4D:
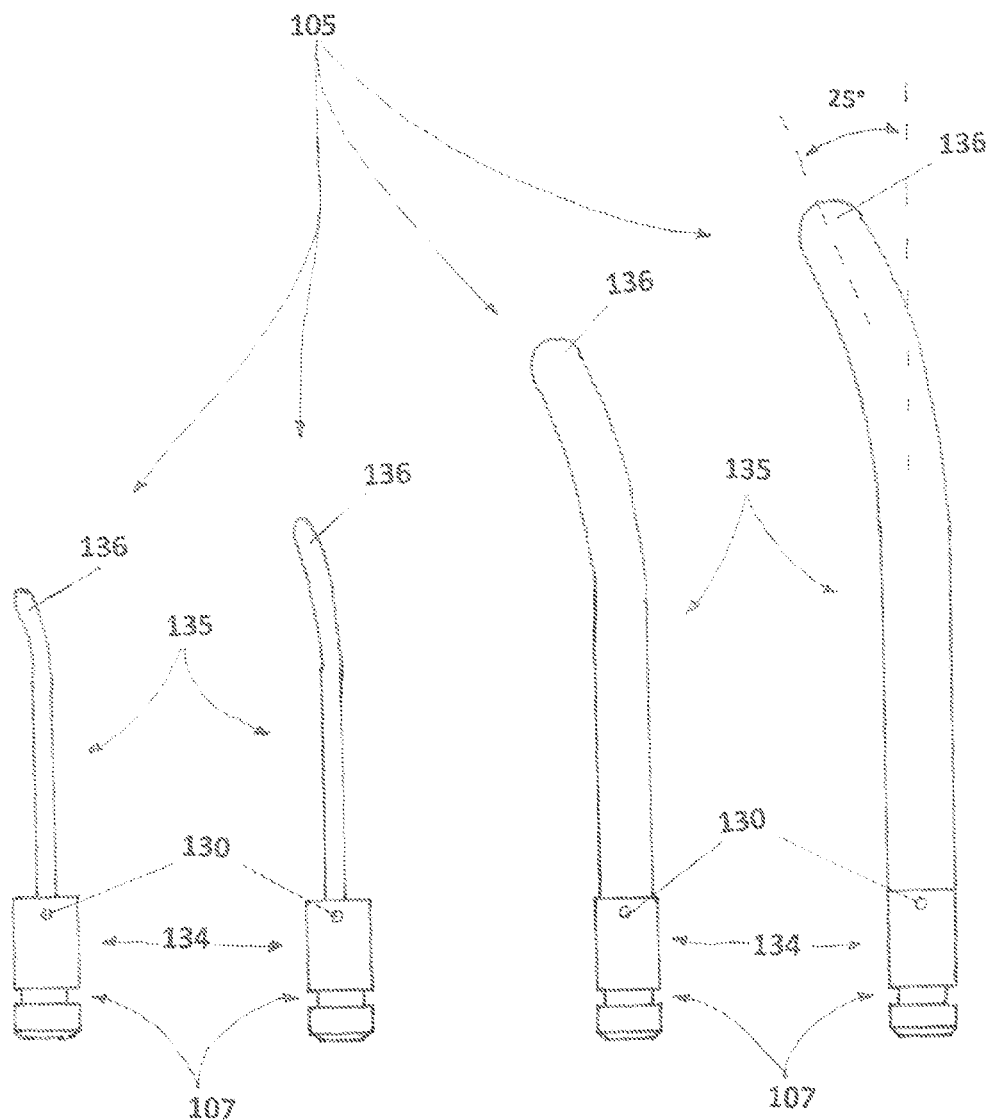
FIG. 4a is a side elevation view of a delineator with a stem 3×45 mm.
FIG. 4b is a side elevation view of a delineator with a stem 3×55 mm.
FIG. 4c is a side elevation view of a delineator with a stem 6×80 mm.
FIG. 4d is a side elevation view of a delineator with a stem 8×100 mm.

The vaginal delineating device consists of: a vaginal delineator 100, shown on FIG. 1a-1d. The vaginal delineator has three different sizes. Small, medium (shown on the drawings) and large. The vaginal delineator consists of a solid ring 116, a base 101, and a cylindrical wall 126. The solid ring 116 has an elliptical shape. The major axis is in anterior-posterior direction and the minor axis is perpendicular to it. The minor axis of the solid ring 116 of the medium size vaginal delineator 100, FIG. 1a-1d is preferable 30 mm, of the small size vaginal delineator is preferable 24 mm and of the large size vaginal delineator is preferable 40 mm. In the middle of the outside surface of the solid ring 116 there is an elliptical protrusion 115. Between a proximal rim 114 of the solid ring 116 and the elliptical protrusion 115 is created a guiding groove 122. The solid ring 116 is tilted about 10° degrees anteriorly, for easier insertion into the vagina, FIG. 1b. The larger part of the distal rim 158 of the solid ring 116 is permanently affixed to the proximal end of the cylindrical wall 126. The distal rim 158 of the solid ring 116 anteriorly, on a small distance is not attached to the cylindrical wall 126, it is a free area 140. The distal conical end of the cylindrical wall 126 is permanently attached to the posterior and half of the lateral walls of the base 101. The proximal end of the cylindrical wall 116 has the same inside diameters with the solid ring 116 and the distal end has the same outside diameter with the circumference of the base 101. The distal end of the cylindrical wall 126 is half a circle, conical in shape, gradually diminishing its outside diameter, until it reaches the diameter of the circumference of the base 101. Anteriorly, the cylindrical wall 126, is opened and forms a window 120, between a free area 140 of the solid ring 116, the anterior half of the proximal end of the base 101 and the anterior edges 141 of the cylindrical wall 126. The anterior end 141 of the cylindrical wall starts from the solid ring and runs toward the base, forming an arc, opened anteriorly.

The construction and dimensions of the base 101 of the three delineators are the same. The base 101 of the vaginal delineator has an extension 118, FIG. 1b-1d, which is inserted into the hole 151 of the elastic diaphragm 138, FIG. 11a and 11c. Through the center of the base 101, and the extension 118 there is a hole 102, running from the proximal end of the base 101 towards the distal end of the extension 118. Inside the hole 102 there is a circular groove 121, FIG. 1d, for insertion of an 'O' ring (not shown). The purpose of the "O" ring is to prevent leak of carbon dioxide between a cannula's locking end 103 or an obturator's locking end 134 and the wall of the hole 102. On the distal end of the extension 118, of the base 101 there is a pin 117, FIGS. 1b and 1c. On the proximal surface of the base 101 there is a slot 119, FIG. 1a, which is connected with the hole 102. When through the proximal opening of the hole 102 is inserted a locking end 103, of a cannula 105, FIG. 3a-3d, or a locking end 134 of an obturator 106, FIG. 4a-4d the pin 130 enters the slot 119 of the vaginal delineator 100, this will not allow an obturator or cannula to rotate, but stay in a fixed position, with its bended tip 149 pointing anteriorly, FIG. 8 and FIG. 9. When the locking end is inserted into the head 110 of the uterine mobilizer, the pin 130 enters the slot 123 on the head 110 of the mobilizer, FIG. 9. This prevents rotation of the vaginal delineator, so the window 120 is facing anteriorly.

Figure 12:
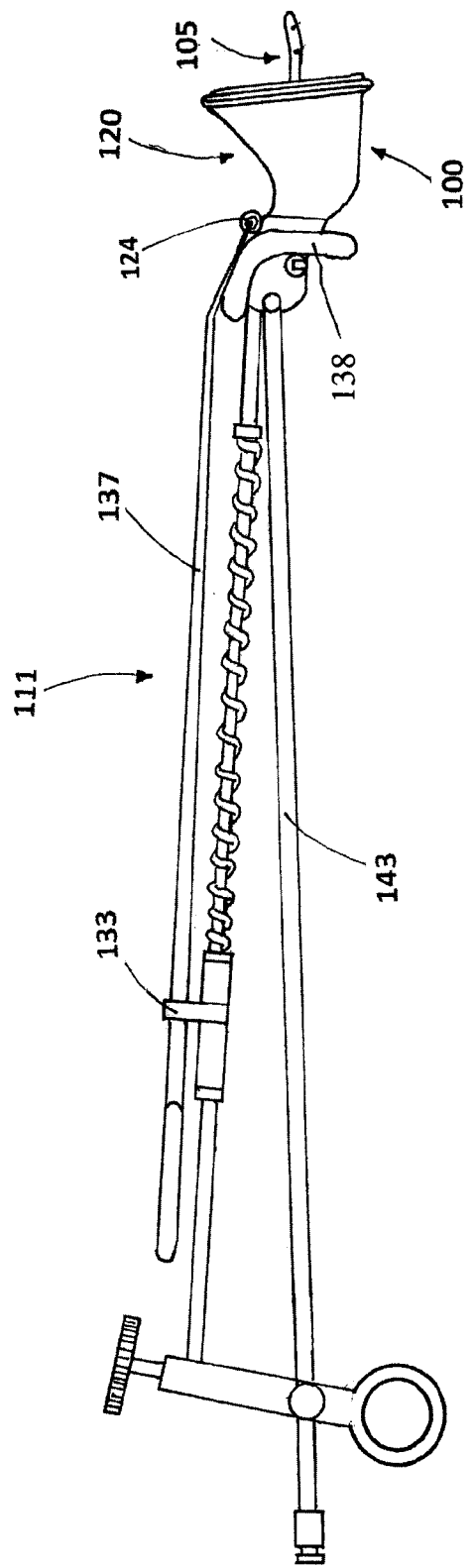
FIG. 12 is a side elevation view of the Valtchev® Uterine Mobilizer with locked in place a delineator, cannula, elastic diaphragm and a tenaculum.
Figure 13:
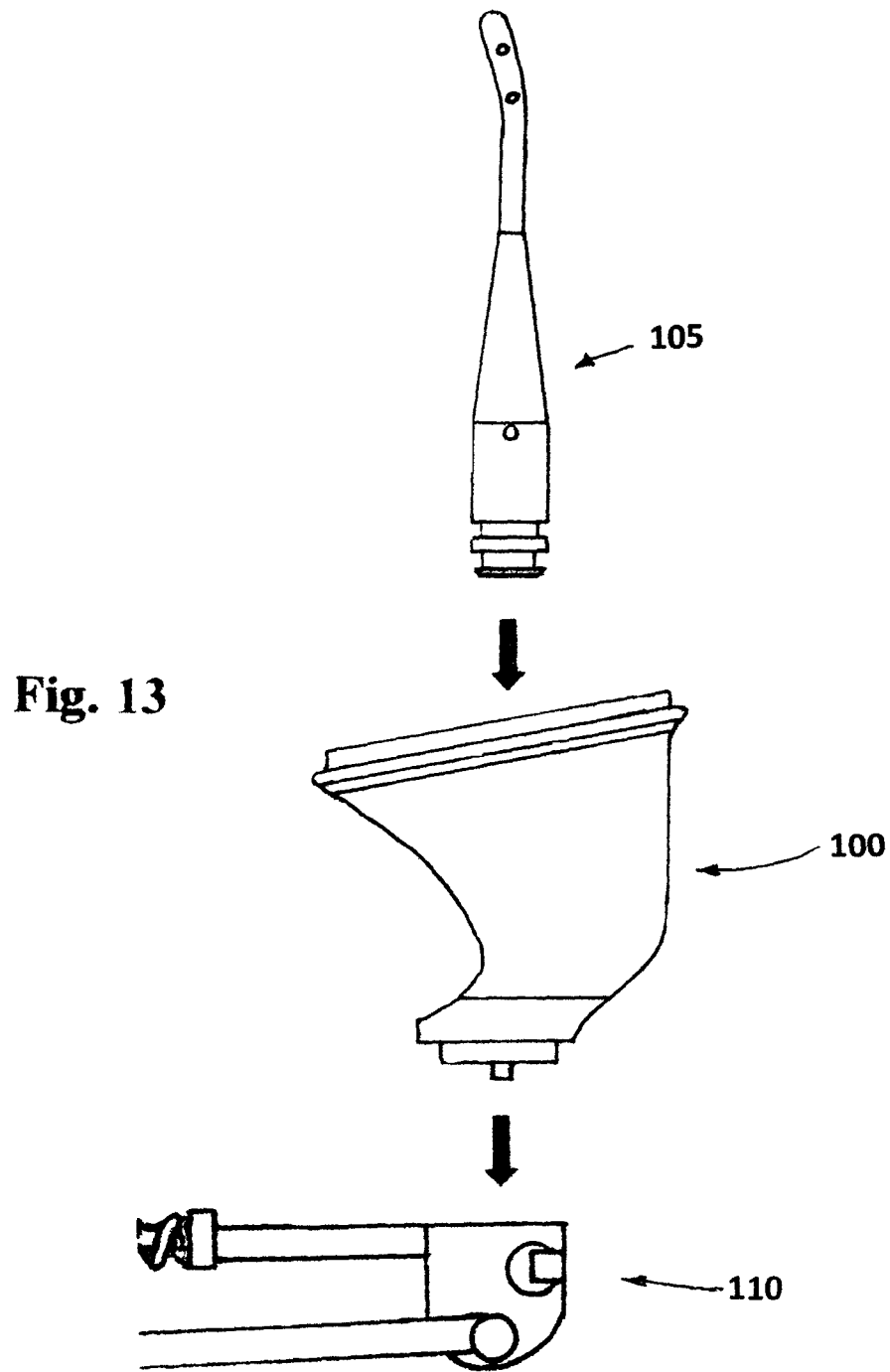
FIG. 13 is a side elevation view of the head of the Valtchev® Uterine Mobilizer, a vaginal delineator and a cannula the way they are to be assembled.

A loop 124, is permanently affixed, in the middle, on the anterior surface of the base 101. The axis of the opening 127 of the loop 124 is perpendicular to the axis of the vaginal delineator 100. The loop 124 can be used to attach a tenaculum 137, which after it is inserted and locked into the tenaculum holder 133, FIG. 12, bends the proximal end of an elastic diaphragm 138 toward the Valtchev® Uterine Mobilizer 111, eliminating visual obstruction toward the window 120 of the vaginal delineator 100. This facilitates the insertion of a cannula 105 or an obturator into the uterine cavity 144, FIG. 10. Through the opening 127 of the loop 124 a suture 155 holding the cervix can be treaded and tied, attaching in this way the cervix 146 to the vaginal delineator 100.

Figure 6:
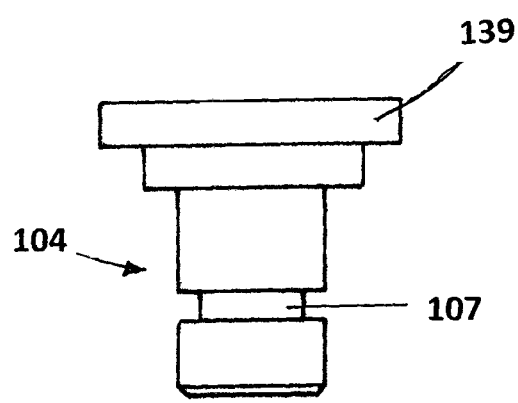
FIG. 6 is a side elevation view of the delineator lock.
Figure 7:
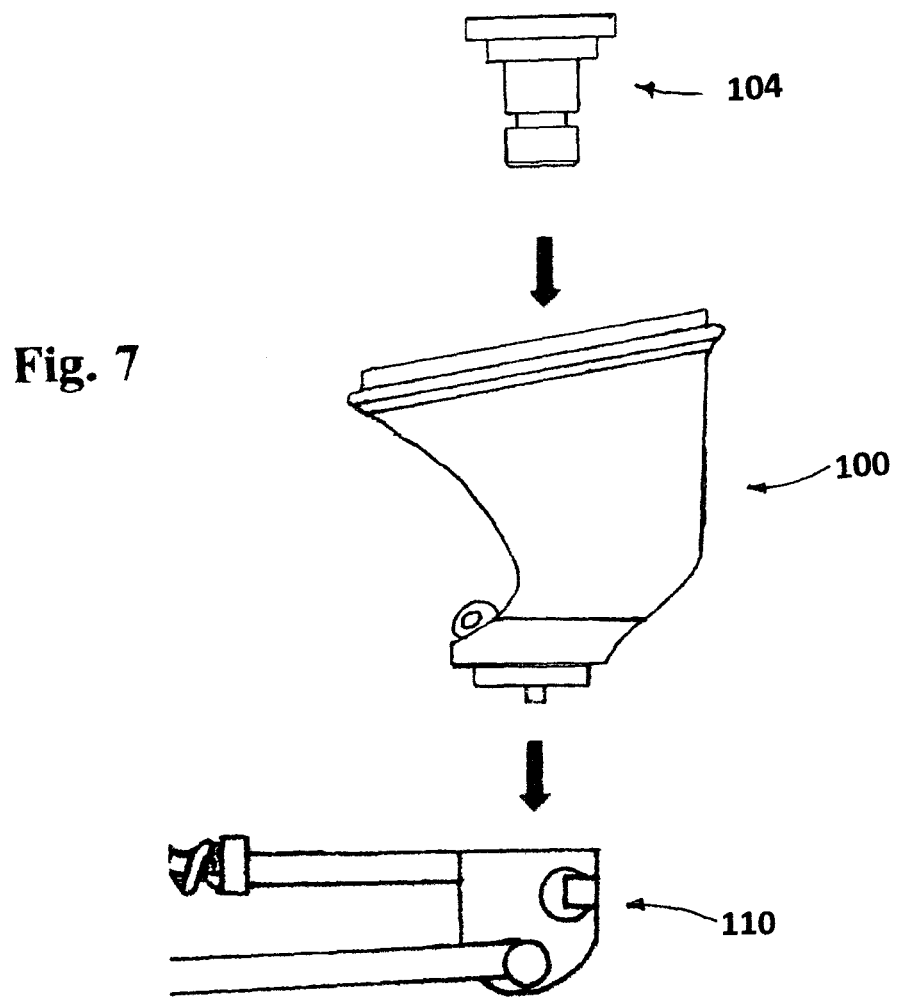
FIG. 7 is a side elevation view of the head of the Valtchev® Uterine Mobilizer, a vaginal delineator and a delineator lock, the way they are to be assembled.

The vaginal delineator lock 104, FIG. 6 and FIG. 7, has a grasping plate 139, for easy insertion and removal. The vaginal delineator lock 104 has a proximal groove 107 which engages a pin 125 of the head lock 109 of the Valtchev® Uterine Mobilizer, FIG. 9. When the use of a cannula or an obturator are not necessary, the vaginal delineator can be attached to the uterine mobilizer by the vaginal delineator lock.

There are four cannulas 105, for injection of fluids, FIG. 3a-3d. Two of them FIG. 3a and FIG. 3b have a small cone 128 the other two, have a large cone 129, FIG. 3c and FIG. 3d. The cannulas with a small cone FIGS. 3a and 3b, are for nuliparous women (those who have not delivered a baby). The cannulas with a large cone FIG. 3c and FIG. 3d are to be used on parous women. The distal end of the large cone cannulas is knurled 132 for easy handling. The locking end 103 of the cannulas 105 has the same dimensions and construction. A distal groove 108, FIG. 3a-3d, accommodates an 'O' ring (not shown) and a proximal groove 107 engages the pin 125 of the head lock 109 of the uterine mobilizer, FIG. 9. The "O" ring for the distal groove 108 prevents leak of fluid when such is injected through the tube 131 of the mobilizer, FIG. 9. The cannulas 105 have a distal opening 112 through which fluid enters a canal 157 of the cannula 105 and exits through four proximal openings 113, on the side wall of the tube, two on one side and two on the opposite side of the tube 131, FIG. 3c. The tubes 131 of the cannulas 105 are permanently affixed to the tip of the cone. The outside diameter of the tube is preferable 3 mm. have preferable 3 mm. The tubes at the tips 149 are closed, and bended about 20° anteriorly. The preferable length of the two short cannulas FIGS. 3a and 3c are 60 mm, and the remaining two long cannulas, FIG. 3b, and FIG. 3d, are preferably 70 mm. in length.

There are four obturators 106, FIG. 4a-4d. The stems 135 of the obturators 106 may have different length, to fit the different length of the uterine cavity. We prefer 45 mm FIG. 4a, 55 mm FIG. 4b, 80 mm FIG. 4c and 100 mm FIG. 4d, length. The stems 135 of the two obturators, FIG. 4a and 4b have preferable outside diameter of 3 mm. The stem 135 of the obturator FIG. 4c has outside diameter preferably 8 mm and the stem 135 of the obturator FIG. 4d has outside diameter preferable 10 mm. The stems at the tips 136 are bended about 25° anteriorly. The locking end 134 of all obturators 106 have the same dimensions and construction. They have a proximal groove 107, which engages the pin 125 of the head lock 109 of the uterine mobilizer.

Figure 11A:
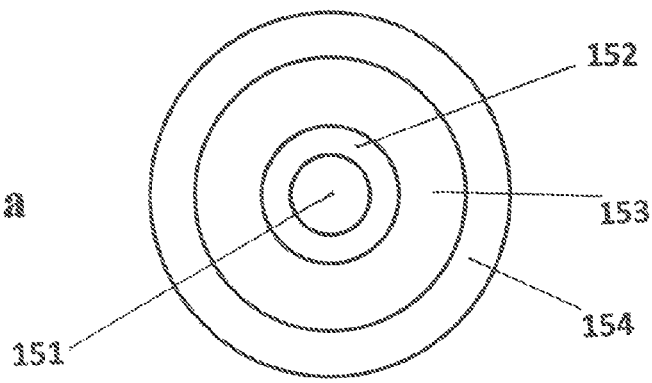
FIG. 11a is a plan view from the top of the elastic diaphragm.
Figure 11B:
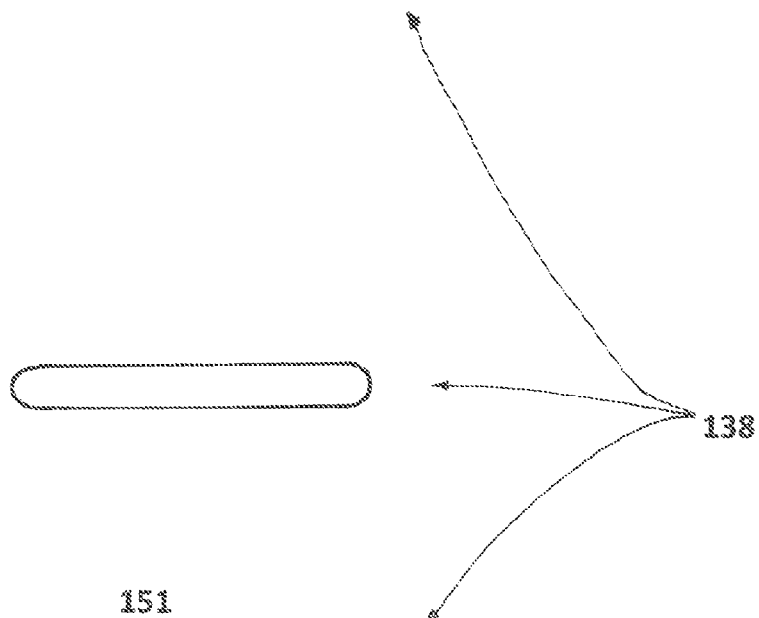
FIG. 11b is a side elevation view of the elastic diaphragm.
Figure 11C:
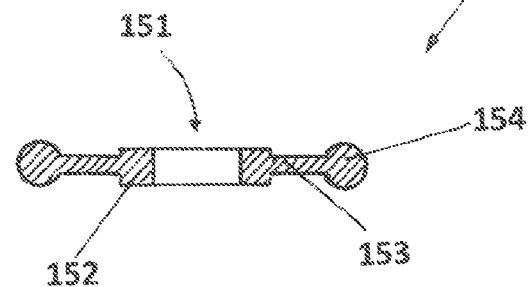
FIG. 11c is a cross section of the elastic diaphragm.

An occluding device comprising an elastic diaphragm 138, FIG. 11a-11c, has a hole 151 in the center of an annulus 152, through which an extension 118 of the base 118, FIG. 1b and FIG. 1d, of the vaginal delineator 100 passes. A rim 154 and the annulus 152 of the elastic diaphragm 138 are thicker than the membrane 153, FIG. 11a-11c.

Figure 5:
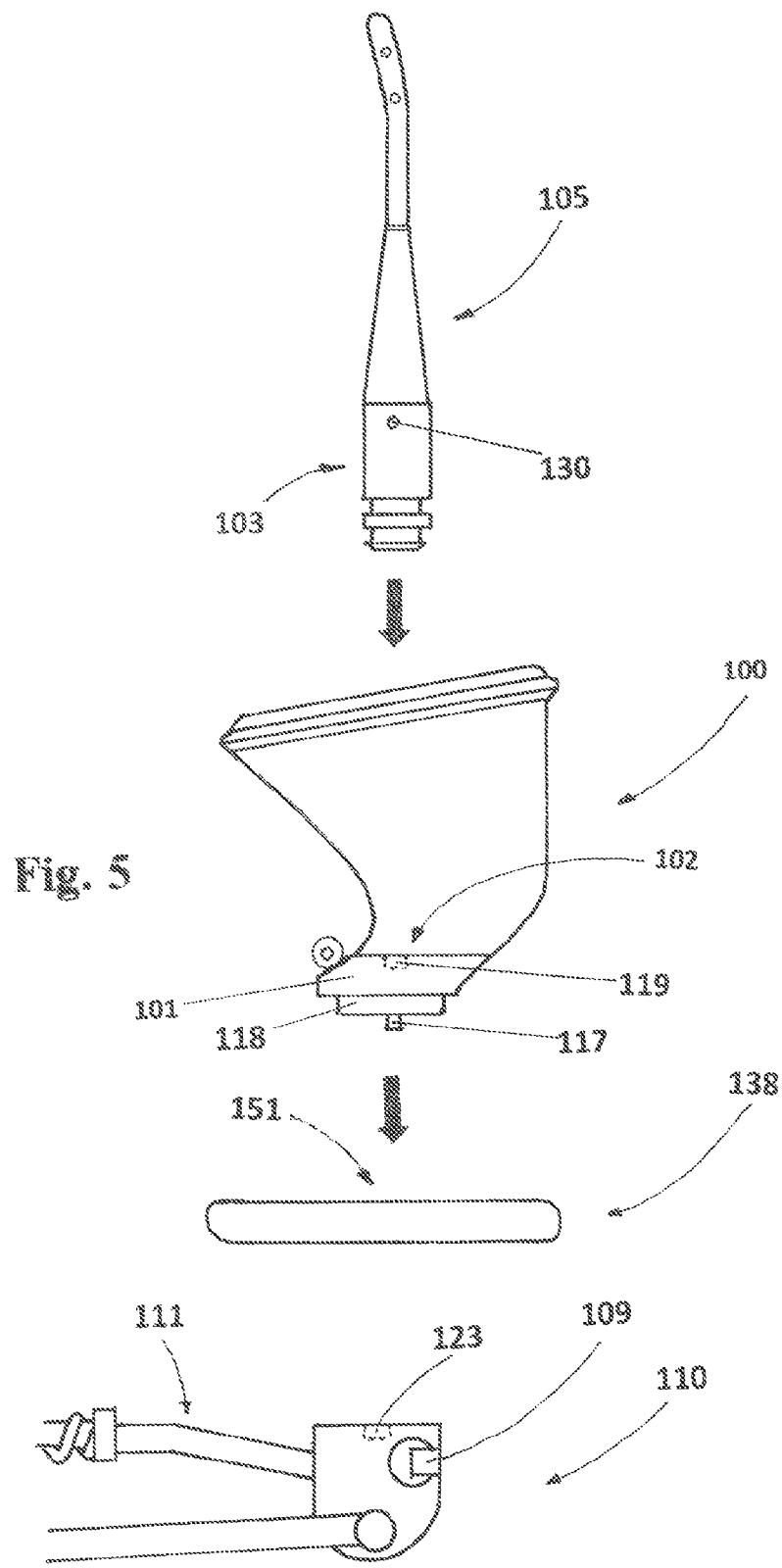
FIG. 5 is a side elevation view of the head of the Valtchev® Uterine Mobilizer, an elastic diaphragm, a vaginal delineator and a cannula, the way they are to be assembled.

On FIG. 5 is shown the way of assembling and locking into the head 110 of the Valtchev® Uterine Mobilizer 111, an elastic diaphragm 138, a vaginal delineator 100 and a cannula 105. First the locking end 103 of a cannula 105 is inserted through the proximal end of the hole 102 of the base 101, of the vaginal delineator 100, the pin 130 engages the slot 119 of the vaginal delineator 100. The extension 118 of the base is inserted into the hole 151 of the elastic diaphragm 138 and finally the distal end of the locking end 103 of the cannula is inserted into the head 110 of the uterine mobilizer 111, so that the pin 117 of the cannula 105 enters the slot 123 on the head 110 of the uterine mobilizer, FIG. 5, FIG. 8 and FIG. 9. At this point the proximal groove 107 of the cannula is aligned with the pin 125 of the head lock 109 which locks the assembled parts in place, FIG. 9 and FIG. 10. As it is obvious, the two pins entering the corresponding slots do not permit rotation of the vaginal delineator and the cannula. The window 120 of the vaginal delineator and the bended tip of the cannula are aligned with the longitudinal axis of the mobilizer and pointing anteriorly, FIG. 8 and FIG. 9.

Figure 10:
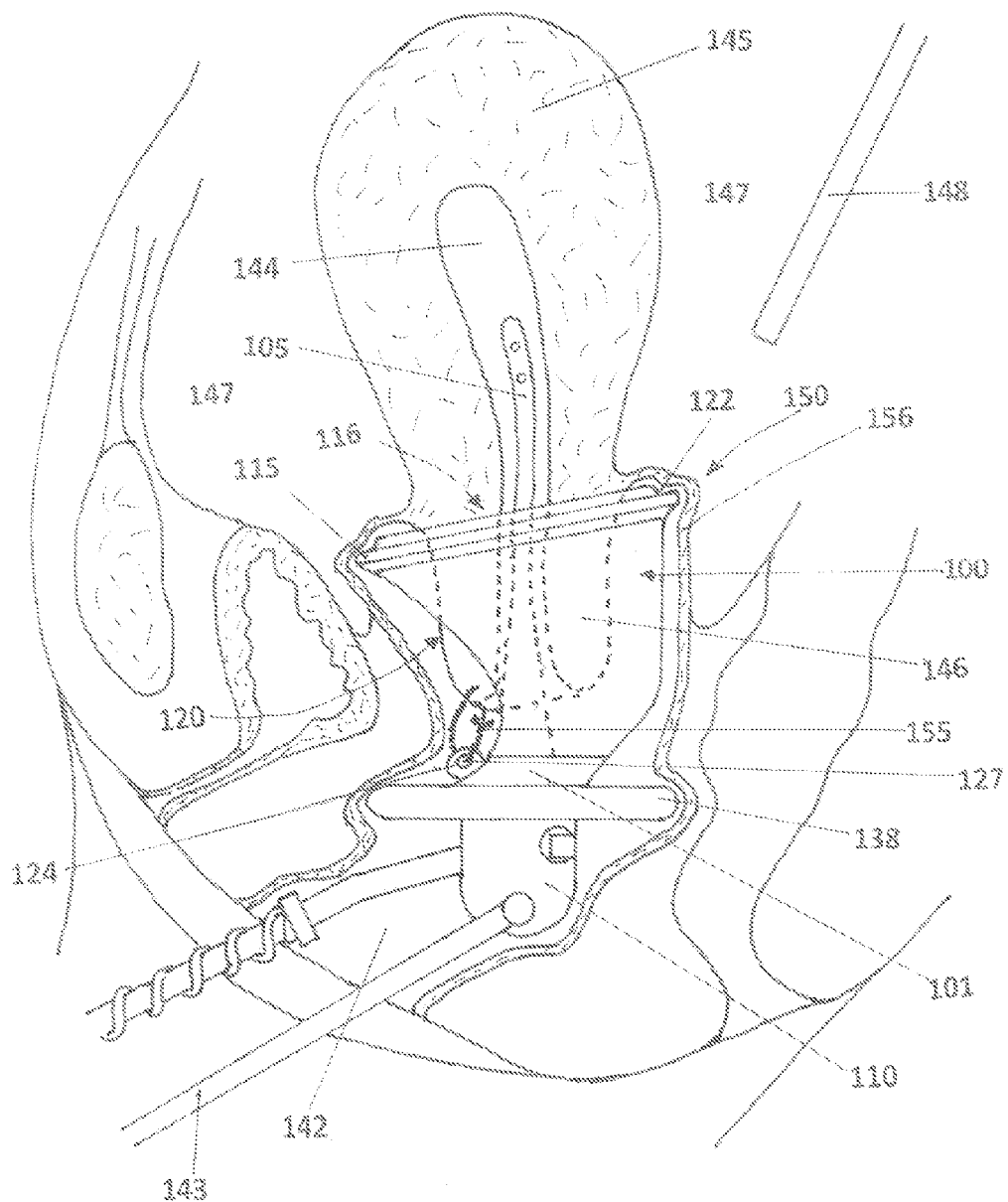
FIG. 10 is a cutaway view of a female pelvis, a side elevation view of the vaginal delineator, a cannula and a elastic diaphragm, being inserted and locked into the head of the Valtchev® Uterine Mobilizer, the cannula is inserted into the uterine cavity and the vaginal delineator and the elastic diaphragm into the vagina.

When the locking end 103 of a cannula or the locking end 134 of an obturator 106 is inserted into the head of the uterine mobilizer and locked in place, the annulus 152 of the elastic diaphragm 138 is held securely between the base 101 and the head 110 of the uterine mobilizer preventing flow in any direction, FIG. 10. Various sizes of the elastic diaphragm 138 may be supplied to fit a variety of vaginal diameters. Our preferable sizes are 55 mm, 70 mm, 75 mm and 80 mm in diameter. On FIG. 7 is shown an assembling and locking of a vaginal delineator 100, by a delineator lock 104. This assembly is used when there is not a uterus, or insertion of an obturator or cannula for some reason is impossible or not desired.

Figure 8:
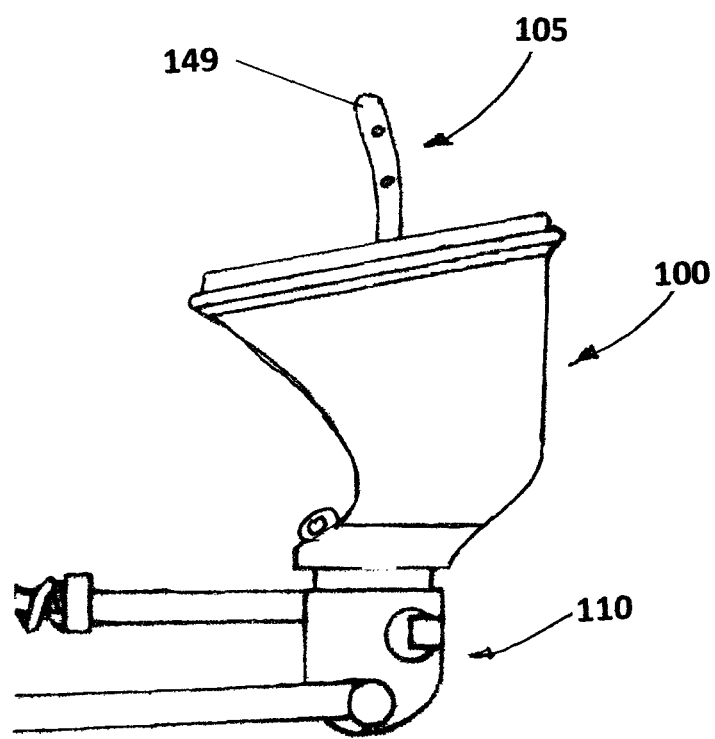
FIG. 8 is a side elevation view of an assembled vaginal delineator and cannula locked into the head of the Valtchev® Uterine Mobilizer.
Figure 9:
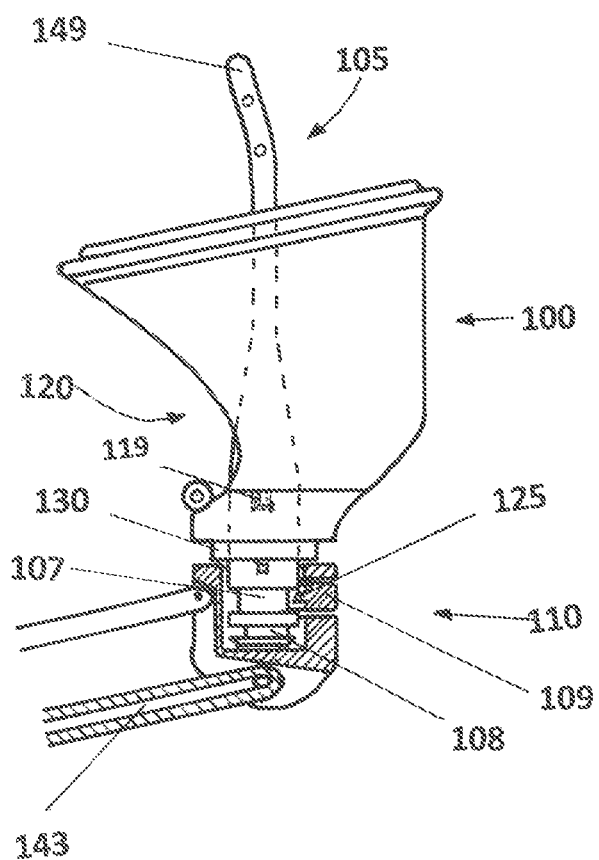
FIG. 9 is a side elevation view of an assembled vaginal delineator, cannula and cutaway view of the head of the Valtchev® Uterine Mobilizer.

On FIG. 8 is shown already assembled a vaginal delineator 100 and a cannula 105. An elastic diaphragm 138 is not used, because the vagina is not going to be opened laparoscopically.

On FIG. 10 is shown the vaginal delineator 100 with a cannula 105 and an elastic diaphragm 138 inserted into the vagina 142 and the uterine cavity 144. The elliptical protrusion 115 of the solid ring 116 push the vaginal wall 156 toward the abdominal cavity 147 and forms a circular bulging 150, easily visible through a laparoscope 148. The guiding groove 122, guides the cutting instrument during colpotomy. The elastic diaphragm 138 stretches the vaginal wall 156 and obstructs a flow in any direction.

The above embodiments are the preferred embodiments, but this invention is not limited thereto. It is therefore, apparent that many modifications and variations of the present invention are possible in the light of the above teaching. It is, therefore, to be understood that within the scope of the appended claims, the invention may be practiced otherwise than as specifically described.

I claim:

1. A method of constructing a vaginal delineating device comprising:
    providing said vaginal delineating device comprising a solid ring, a cylindrical wall, and a base;
    securely attaching the vaginal delineating device to a uterine mobilizer by inserting a cannula, an obturator or a vaginal delineator lock through the vaginal delineating device into the uterine mobilizer; and
    mechanically locking the vaginal delineating device to the uterine mobilizer;
    wherein the solid ring includes:
    (a) an elliptical shape;
    (b) an elliptical protrusion in an outside surface;
    (c) a guiding groove between a proximal rim and the elliptical protrusion; and
    (d) a solid distal rim of the solid ring permanently affixed to a proximal end of the cylindrical wall, excluding a small area anteriorly.

2. The method of claim 1 wherein the solid ring is tilted anteriorly about 10° toward a longitudinal axis of the vaginal delineating device.

3. The method of claim 1 wherein the cylindrical wall comprises:
    (a) a distal end conical in shape;
    (b) the distal end being formed in approximately a half circle; and
    (c) the distal end permanently affixed to the posterior and lateral proximal end of the base.

4. The method of claim 3 wherein the cylindrical wall additionally comprises:
    (a) an inside diameter of the proximal end having the inside diameter of the solid ring;
    (b) an outside diameter of the distal end having the outside diameter of the base; and
    (c) anterior edges of the cylindrical wall form an arch, open anteriorly.

5. The method of claim 1 wherein the base comprises:
 (a) a posterior and half of the lateral proximal end being permanently affixed to the distal circular end of the cylindrical wall;
 (b) an extension of the base, for receiving a hole of an elastic diaphragm; and
 (c) a hole through the center of the base and the extension, for receiving a locking end of the obturator, the cannula or the vaginal delineator lock.

6. The method of claim 5 wherein the base additionally comprises:
 (a) a loop permanently affixed in the middle of the anterior surface of the base, the loop including an opening;
 (b) an axis of the opening of the loop being disclosed perpendicular to the axis of the vaginal delineator; and
 (c) a tenaculum or suture being attached through the opening of the loop.

7. The method of claim 6 wherein the base additionally comprises:
 (a) a slot on the proximal surface connected to the hole, for receiving a pin of an obturator or a cannula;
 (b) a circular groove inside the hole for housing an "O" ring; and
 (c) a pin on the distal end of the extension of the base for engaging the slot on the head of the uterine mobilizer.

8. The method of claim 6 wherein the loop additionally comprises:
 (a) a tenaculum attached to the loop and to a tenaculum holder of the uterine mobilizer disposed to bend the proximal end of the elastic diaphragm toward the mobilizer;
 (b) a bent elastic diaphragm disposed to eliminate visual obstruction toward the window; and
 (c) a suture through the loop and the cervix disposed to attach securely the cervix to the vaginal delineator.

9. A method of claim 1 wherein the vaginal delineator additionally comprises: a single window in the anterior part of the vaginal delineator between a free part of the solid ring, anterior half of the proximal end of the base and the anterior edges of the cylindrical wall.

10. The method of claim 1 wherein the cannula for injection of fluid into the uterine cavity comprises:
 (a) a tube permanently affixed to a tip of a cone;
 (b) a tube at the tip being closed and bent about 20° anteriorly; and
 (c) four openings on the side wall of the tube, two on one side and two on the opposite side.

11. The method of claim 10 wherein the cannula additionally comprises a canal for injection of fluids.

12. The method of claim 1 wherein the said cannula additionally comprises:
 (a) a cone;
 (b) a tube; and
 (c) a locking end at the distal end of the cone for securing the vaginal delineator to the uterine mobilizer.

13. The method of claim 12 wherein the locking end additionally comprises:
 (a) a pin on the proximal end of the locking end disposed to engage a slot on the proximal surface of the vaginal delineator;
 (b) a proximal groove disposed to engage the locking pin of a head lock of the uterine mobilizer; and
 (c) a distal groove for housing an "O" ring, preventing flow in any direction.

14. The method of claim 1 wherein the obturators comprise:
 (a) a stem;
 (b) wherein the stem is bent at the tip to about 25° anteriorly; and
 (c) a locking end permanently affixed to the distal end of the stem.

15. The method of claim 14 wherein the locking end of the obturator comprises:
 (a) a pin at the proximal end for engaging a slot on the proximal surface of the vaginal delineator; and
 (b) a proximal groove engaging the locking pin of the head lock of the uterine mobilizer.

16. The method of claim 1 wherein the vaginal delineator lock attaching and locking the vaginal delineator to the uterine mobilizer comprises:
 (a) a locking end for insertion into the hole of the vaginal delineator and into the head of the uterine mobilizer;
 (b) a proximal groove disposed to engage the pin of the head lock of the uterine mobilizer; and
 (c) a grasping plate for handling the vaginal delineator lock.

* * * * *